United States Patent [19]

Alexander

[11] Patent Number: 4,514,510

[45] Date of Patent: Apr. 30, 1985

[54] HYDROGEN ENRICHED WATER SWELLABLE CLAY HAVING REDUCED ACID DEMAND AND STABLE AT LOW PH

[75] Inventor: William Alexander, Naperville, Ill.

[73] Assignee: American Colloid Company, Skokie, Ill.

[21] Appl. No.: 530,430

[22] Filed: Sep. 8, 1983

[51] Int. Cl.³ .................... B01J 13/00; C04B 33/04
[52] U.S. Cl. .................... 501/148; 501/146; 252/313.1; 252/315.5
[58] Field of Search .............. 252/313 R, 315.5; 501/148, 146; 424/357

[56] References Cited

U.S. PATENT DOCUMENTS 2,431,481 11/1947 Hurd et al. .............. 252/315.5
2,905,643 9/1959 Billue et al. .............. 252/313 R

FOREIGN PATENT DOCUMENTS 521741 2/1956 Canada .............. 252/313 S

*Primary Examiner*—Richard D. Lovering

*Attorney, Agent, or Firm*—Mason, Kolehmainen, Rathburn & Wyss

[57] ABSTRACT

A water swellable clay i.e. bentonite, hectorite, saponite or mixtures thereof, is slurried in water and contacted with a hydrogen ion exchange resin to replace a portion of the exchangeable sodium and other exchangeable cations with hydrogen, resulting in a hydrogen enriched, water swellable clay. It has been found that even the very low grade water swellable clays can be treated with the hydrogen ion exchange resin to provide a hydrogen enriched clay having reduced acid demand. The resulting clays have reduced acid demand for mixture in forming Magnesium Aluminum Silicate meeting specifications. Further, the resulting hydrogen enriched clay will not substantially flocculate or settle out of suspension in suspensions having a pH below about 6.0 and generally are useful in a suspension having a pH of about 2.0 to about 5.0 or about 2.0 to about 5.5 so that the modified clay can be used effectively as a suspending agent and as a viscosity modifying agent in water containing suspensions having a low pH.

19 Claims, No Drawings

HYDROGEN ENRICHED WATER SWELLABLE CLAY HAVING REDUCED ACID DEMAND AND STABLE AT LOW PH

FIELD OF THE INVENTION

The present invention is directed to a modified, hydrogen enriched water swellable colloidal clay and a method of manufacturing the modified hydrogen enriched clay. More particularly, the present invention is directed to a hydrogen enriched clay composition manufactured by contacting one or more clays with a hydrogen ion exchange resin to replace a portion of exchangeable clay cations with hydrogen resulting in a hydrogen enriched clay capable of meeting specifications for Magnesium Aluminum Silicate and having new and unexpected stability in compositions having a pH below about 6.0.

BACKGROUND OF THE INVENTION AND PRIOR ART

Specifications for materials used in pharmaceutical and cosmetic compositions must meet rigid specifications (official monographs) described, for example, in the U.S. Pharmacopeia XX and National Formulary XV. Magnesium Aluminum Silicate, sold by R. T. Vanderbilt Co. in the pharmaceutical and cosmetic industry, i.e. for use in anti-dandruff shampoo, has very rigid and narrow monographs, apparently derived from a rare clay, mined by R. T. Vanderbilt from a location miles under ground level. A combination of the rare clay with other clays meets the official monograph for magnesium aluminum silicate since the rare clay does not contain any significant amount of contamination, such as calcite (calcium carbonate) or dolomite (calcium manesium carbonate).

The official monograph for Magnesium Aluminum Silicate is written very narrowly for pH, viscosity, Aluminum/Magnesium ratio and acid demand so that prior to the present invention, it has been impossible to meet the official monograph without including at least a portion of the R. T. Vanderbilt rare, uncontaminated clay in the Magnesium Aluminum Silicate composition.

The official monograph for Magnesium Aluminum Silicate defines the material as "a colloidal montmorillonoid saponite, in which magnesium has substantially replaced aluminum in the crystal lattice, that has been processed to remove grit and non-wettable ore components."

Previous attempts by this assignee to wash and otherwise process contaminated clays in an attempt to meet the official monograph for Magnesium Aluminum Silicate have been unsuccessful. Consequently, prior to the present invention, R. T. Vanderbilt Co. has been the only supplier of Magnesium Aluminum Silicate to the pharmaceutical and cosmetics industries.

The specification for Al/Mg ratio is achieved by blending together a dioctahedral montmorillonite clay with saponite, sepiolite, talc and/or hectorite (trioctrahedral clay). Saponite, sepiolite, talc and hectorite each include very little or no aluminum and a significant amount of magnesium in the form of magnesium oxide; and dioctahedral montmorillonites, such as bentonite, have little or no magnesium and a significant amount of aluminum in the form of aluminum oxide. Any required Al/Mg ratio can be achieved by blending the montmorillonite with saponite and/or hectorite. However, the specifications for Magnesium Aluminum Silicate call for very specific viscosity and acid demand requirements as follows:

Viscosity—After determining the Loss on drying, weigh a quantity of Magnesium Aluminum Silicate test specimen equivalent to 25.0 g on the dried basis. Over a period of a few seconds, transfer the undried test specimen to a suitable 1-liter blender jar containing an amount of water, maintained at a temperature of 25°±2° C., that is sufficient to produce a mixture weighing 500 g. Blend for 3 minutes, accurately timed, at 14,000 to 15,000 rpm (high speed). (Note-Heat generated during blending causes a temperature rise to above 30°.) Transfer the contents of the blender to a 600-ml beaker, allow to stand for 5 minutes and adjust, if necessary, to a temperature of 33°±3°. Using a suitable rotational viscometer, operate the viscometer for 6 minutes, accurately timed, and record the scale reading. Convert the scale reading to centipoises by multiplying the reading by the constant for the viscometer spindle and speed employed.

| Type | Viscosity (cps) Min. | Viscosity (cps) Max. | Al content/Mg content Min. | Al content/Mg content Max. |
| --- | --- | --- | --- | --- |
| 1A | 225 | 600 | 0.5 | 1.2 |
| 1B | 150 | 450 | 0.5 | 1.2 |
| 1C | 800 | 2200 | 0.5 | 1.2 |
| 11A | 100 | 300 | 1.4 | 2.8 |
| 111A | 250 | 500 | 3.5 | 5.5 |
| 111B | 40 | 200 | 3.5 | 5.5 |

Acid demand—After determining the loss on drying, weigh a quantity of Magnesium Aluminum Silicate equivalent to 5.00 g, and disperse in 500 ml of water with the aid of a suitable blender fitted with a 1-liter jar. Using a stopwatch, designate zero time. With consant mixing, add 3.0-ml portions of 0.100 N hydrochloric acid at 5, 65, 125, 185, 245, 305, 365, 425, 485, 545, 605, 665, and 725 seconds, and add a 1.0-ml portion at 785 seconds. Determine the pH potentiometrically at 840 seconds: the pH is not more than 4.0.

The lower the Al/Mg ratio required for a particular type of Magnesium Aluminum Silicate, the more hectorite and/or saponite required. Too much hectorite increases viscosity beyond specifications and too much saponite causes stability problems, as determined by any separation of a slurry of the material in water upon standing about 24 hours. If all three clays do not contain any significant contamination, it is possible to blend the montmorillonite and hectorite or montmorillonite and saponite or all three types of clay to achieve the desired specifications. If any of the clays contain non-clay minerals such as calcite (calcium carbonate) or dolomite (calcium magnesium carbonate), however, the clay composition will probably fall out of specification for acid demand. At a pH below about 6, the carbonate will convert to carbon dioxide, generating gas and the pH will buffer back above the pH 4 acid demand specification.

Acid demand is an extremely difficult requirement to meet while maintaining the required Al/Mg ratio. In accordance with the specifications, after incremental additions of 40 ml. of 0.1 N HCl, the pH of the material must be 4.0 or less. Almost all available hectorite and saponite contain sufficient contamination to fall out of specification for acid demand when combined with commonly available montmorillonite. The hectorite is contaminated with calcite and the saponite is contaminated with dolomite. Also, the montmorillonite, as mined, generally has little or no sodium so it becomes necessary to add sodium carbonate to convert the clay from its non-colloidal state to a colloidal clay. The added carbonate in the treated montmorillonite contributes to the acid demand problem.

Attempts to form a blend of 70% montmorillonite, 20% hectorite and 10% saponite to achieve an Al/Mg. ratio of 1.0 results in a Magnesium Aluminum silicate which does not meet the acid demand specification. Five grams of the product includes 0.7(5)=3.5 grams of montmorillonite; 0.2(5)=1.0 gram of hectorite; and 0.1(5)=0.5 gram of saponite per 500 milliliters of water. The montmorillonite required 27 milliliters of 0.1 N HCl to reduce the pH to 4.0; the hectorite required 13 milliliters to reduce the pH to 4.0; and the saponite required 3 milliliters for a total of 43 milliliters. The specification calls for a pH of 4.0 or less upon the addition of 40 milliliters of 0.1 N HCl.

One might suspect acid demand could be met if the blend ratios were changed. For example, since the saponite only requires 3 milliliters of acid to lower the pH to 4.0, conceivably one could add more saponite and less hectorite to meet acid demand. However, since the saponite is acid treated, by increasing the amount of saponite, the final product would fall out of specification for pH, which is 9-10. Also, due to the excess acid in the saponite, an acid stability problem would result. Further, lowering the amount of sodium carbonate treatment of the montmorillonite would lower the acid demand within specifications, but then the added sodium would be insufficient to convert the clay to a colloidal state and, therefore, the product would not meet viscosity specifications.

The product needs hectorite and/or saponite to meet the aluminum/magnesium ratio. If the product contains all hectorite, however, the viscosity would be out of specification because hectorite has a very high viscosity. Hectorite also contributes to the acid demand problem. Saponite, can be blended with hectorite to meet the Al/Mg ratios, but too much saponite causes the pH to be out of specification and creates acid stability problems. Sodium carbonate treatment is needed for the contaminated montmorillonite, even if thoroughly washed, to achieve a colloidal clay. The carbonate treatment of the montmorillonite contributes to an acid demand problem and also increases the pH so that the final product could fall out of specification for pH. Because of all these problems, specifications for Magnesium Aluminum Silicate have been very difficult, if not impossible, to meet.

Further, in many cosmetic and pharmaceutical suspensions, i.e. antiperspirant compositions, it is necessary for the purpose of stability or other reasons that the suspension have a relatively low pH in the range of about 2.0 to about 5.0. Bentonite clay alone slurried in water will yield a bentonite suspension having an alkaline pH, normally with the range of about 8.5 to about 11.0 or 12.0 using quantities of bentonite typical in the manufacture of cosmetic and pharmaceutical suspensions. The addition of one or more acids, for example hydrochloric or phosphoric acid to a bentonite clay slurry to achieve a pH in the range of about 2.0 to about 5.0, or 5.5, and generally below about 6.0, has caused typical bentonite suspensions to lose its suspending capacity, resulting in flocculation and settling of the bentonite from the suspension. Accordingly, prior to the present invention, only very pure grades of bentonite, i.e. white bentonite, having very few impurities could be used in a water suspension having a pH below about 6.0 without the formation of precipitates.

Prior to the present invention, bentonite clays have been modified by ion exchange resins to increase the sodium content or to exchange one polyvalent cation for another on the clay, but prior to the present invention no one has enriched bentonite with hydrogen by contact with a hydrogen ion exchange resin for the purpose of manufacturing a hydrogen enriched clay having reduced acid demand and capable of excellent stability in a water containing suspension having a pH below about 6.0, i.e., 2.0 to 5.5. The following patents disclose ion exchange of clays to provide a sodium enriched clay, or to exchange one polyvalent ion for another on the clay structure: U.S. Pat. Nos. 2,404,038 to Cardwell; 3,158,579 to Pollitzer et al.; 3,993,500; 4,028,133; and 4,047,738 to Issac et al. and U.S. Pat. No. 4,271,043 to Vaughan et al.

SUMMARY OF THE INVENTION

In brief, the present invention is directed to a hydrogen enriched water swellable clay and a method of enriching the water swellable clay with hydrogen by contacting a water suspension of the clay while partially or completely hydrated, with a hydrogen ion exchange resin in an amount and for a time sufficient to provide a modified water swellable clay having a decreased acid demand.

In accordance with the present invention, a water swellable clay i.e. bentonite, hectorite, saponite or mixtures thereof, is slurried in water and contacted with a hydrogen ion exchange resin to replace a portion of the exchangeable sodium and other exchangeable cations with hydrogen, resulting in a hydrogen enriched, water swellable clay. It has been found that even the very low grade water swellable clays can be treated with the hydrogen ion exchange resin to provide a hydrogen-enriched clay having reduced acid demand. The resulting clays have reduced acid demand for mixture in forming Magnesium Aluminum Silicate meeting specifications. Further, the resulting hydrogen enriched clay will not substantially flocculate or settle out of suspension in suspensions having a pH below about 6.0 and generally are useful in a suspension having a pH of about 2.0 to about 5.0 or about 2.0 to about 5.5 so that the modified clay can be used effectively as a suspending agent and as a viscosity modifying agent in water containing suspensions having a low pH.

Accordingly, an object of the present invention is to provide a modified, hydrogen-enriched water swellable clay, particularly montmorillonite clays such as bentonite.

Another object of the present invention is to provide a method of manufacturing a modified, hydrogen-enriched, water swellable clay composition including montmorillonite, hectorite and saponite.

Still another object of the present invention is to provide a modified bentonite clay and a method of manufacturing a modified bentonite clay having an increased H ion concentration as a result of exchange of H ions for other cations initially present on the clay.

Another object of the present invention is to provide a modified, hydrogen-enriched clay, and a method of manufacturing the modified, hydrogen-enriched clay, having new and unexpected properties of stability, suspending and viscosity modifying capacities when slurried in water at a pH below about 6.0 and particularly in the range of about 2.0 to about 5.0 or 5.5.

Still another object of the present invention is to provide a method of suspending solid particles in aqueous compositions by the addition of a modified, hydrogen-enriched water swellable clay thereto.

Another object of the present invention is to provide a method of manufacturing a new and improved hydrogen enriched water swellable clay by ion exchange of the water swellable clay with a hydrogen ion exchange resin, such as a cross linked styrene-divinyl-benzene polymer to provide a clay blend meeting existing specifications for Magnesium Aluminum Silicate.

DETAILED DESCRIPTION OF THE PREFERRED EMBODIMENT

The present invention provides a hydrogen enriched water swellable clay and a new and improved method of manufacturing the clay by hydrogen ion exchange between the clay and a hydrogen ion exchange resin. Generally, any water swellable colloidal clay having cations exchangeable with hydrogen is useful in accordance with the present invention.

As previously described, the clay composition forming Magnesium Aluminum Silicate is a blend of montmorillonite, i.e. bentonite; hectorite; and/or saponite. The hydrogen ion exchange of the present invention is useful in modifying, by acid demand reduction and increase in hydrogen ion concentration, any of the water swellable clays, including any of the montmorillonites, beidellites, nontronites, hectorites and saponites. Generally it is the montmorillonites which require acid demand reduction to meet specification for Magnesium Aluminum Silicate, because of a substantial amount of montmorillonite contamination, even after washing. The montmorillonites generally used have been treated with sodium carbonate to increase the sodium content for the purpose of making the clay colloidal. Accordingly, remaining carbonate which cannot be removed in washing causes a significant increase in acid demand. The present invention, therefore, is most useful in modifying a sodium montmorillonite clay to achieve a lower acid demand and greater stability at low pH.

The modified clay and method of the present invention are extremely useful in the manufacture of a Magnesium Aluminum Silicate composition meeting all specifications (U.S. Pharmacopeia XX and National Formulary XV) for use in the pharmaceutical and cosmetics industries. Reduction in acid demand of a water swellable colloidal clay, particularly reduction in acid demand of montmorillonite and hectorite, permits much more latitude in formulating blends, since acid demand is no longer the bottleneck or limiting specification forcing very limited clay combinations capable of meeting acid demand.

In accordance with one important embodiment of the present invention, the hydrogen ion exchange treated colloidal clay is bentonite. A preferred bentonite is sodium bentonite which is basically a hydratable montmorillonite clay. The clay can include sufficient sodium as mined or can be treated, i.e. peptized, to increase the sodium content. The clay has sodium as a predominant exchange ion and the sodium generally is present in an amount of about 50 to 100 milliequivalents per 100 grams. However, the bentonite utilized in accordance with the present invention may also contain other cations such as calcium, magnesium and iron. The colloidal clay may also be any member of the dioctahedral or trioctahedral smectite group or mixtures thereof. Examples are Beidellite, Nontronite, Hectorite and Saponite. After hydrogen ion exchange, the hydrogen enriched clays of the present invention have a lower acid demand. Hydrogen ion exchange with any of these clays reduces the amount of acid required to lower the pH of a water suspension of the clay to 4.0. The colloidal clay, i.e., bentonite, generally is finely divided as known for use in water barrier panels and the like, i.e, 150 to 350 mesh, to achieve better hydrogen ion exchange, although the clay can be in any form for hydrogen ion exchange to obtain a reduction in acid demand.

In accordance with the present invention, the water swellable clay, for example, bentonite, is contacted with a hydrogen ion exchange resin resulting in a hydrogen enriched water swellable clay having reduced acid demand. A suitable hydrogen ion exchange resin is manufactured by Dow Chemical under the trademark DOWEX and is a cross-linked styrene-divinyl benzene polymer supplied in fully swollen moist bead form having a molecular configuration as follows:

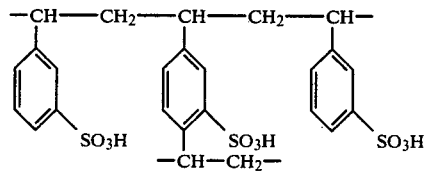

The resin can be regenerated with a strong acid such as sulfuric, hydrochloric or nitric to regenerate the resin to a form capable of substantial hydrogen exchange with a water swellable clay having exchangeable cations. Any hydrogen ion exchange resin capable of liberating H ions for exchange with other cations present on clay can be used in accordance with the principles of the present invention.

Ion exchange may be accomplished by contacting the liquid carrier of the water swellable clay slurry with the hydrogen ion exchange resin at any desired temperature up to about 140° C. Ion exchange generally is carried out at room temperature by passing a water slurry of the clay through a fixed bed of the hydrogen ion exchange resin, or by slurrying the hydrated clay in a slurry containing the hydrogen ion exchange resin until a desired amount of hydrogen has been exchanged for a portion of the exchangeable cations of the clay. Generally, the clay is slurried in water to a clay content of about 1% to about 30% by weight of the water slurry, preferably about 5—15% and thoroughly wetted and mixed for a period of about 1 to 24 hours to assure at least partial swelling or hydration of the clay prior to ion exchange. $Na_2CO_3$ can be added in an amount of, for example, 30 pounds/ton of clay to increase the sodium content to a level within the range of about 50 to 100 meq. of sodium per 100 grams of clay. After thorough mixing and at least partial hydration, in one embodiment, the water slurry is passed by gravity downwardly through a fixed bed of the hydrogen ion exchange resin and may be recirculated through the resin until the desired amount of hydrogen ion exchange is achieved.

In another embodiment, the hydrogen ion exchange resin is added to the at least partially hydrated clay slurry in an amount of about 3–25% based on the weight of the clay. The slurry of clay and hydrogen ion exchange resin is mixed for about 2 hours, or a time necessary to achieve a predetermined degree of ion exchange, or for a time sufficient to achieve a predetermined reduced acid demand. The slurry then is screened to remove the ion exchange resin, centrifuged, and dried, generally to a water content of less than about 10% by weight.

In accordance with one feature of the present invention, the bentonite slurry should contain less than about 30% by weight bentonite based on the weight of clay and water. It has been found that clay concentrations greater than about 30% by weight present problems in centrifuging and screening and require special pumps capable of effective and consistent pumping of slurries containing high solids contents. Further, when a fixed bed of the ion exchange resin is employed, clay concentrations greater than about 30% by weight cause plugging of the fixed bed and frequent shutdowns of the process. Clay slurries having less than about 1% by weight clay are excessively expensive to dry but can be used in accordance with the present invention.

When the hydrogen ion exchange resin is added directly to the hydrated clay slurry, the resin should be added to the slurry of hydrated clay in an amount of at least about 2% based on the weight of the clay to assure that sufficient hydrogen ions are available for exchange with the exchangeable ions of the clay and to avoid prolonged contact times to achieve a desired degree of ion exchange. To achieve the full advantage of the present invention, the ion exchange resin should be added to the hydrated clay slurry in an amount of at least about 4% based on the weight of the clay. The hydrogen ion exchange resin is added to the hydrated clay slurry in an amount of about 4% to about 10% based on the weight of clay to achieve speedy ion exchange. The ion exchange resin can be added in amounts greater than about 10% based on the weight of the clay to achieve faster ion exchange. To determine the amount of ion exchange resin required, the acid demand of the clay composition is measured in accordance with standard testing procedures. A given quantity of ion exchange resin then is added as described, to treat the clay and the acid demand is thereby lowered to a given value, as measured. The amount of ion exchange resin then is adjusted per weight of clay composition to increase or decrease the acid demand of the treated clay. By this slight trial and error, a correct amount of ion exchange resin is determined to achieve a predetermined acid demand for the clay composition.

Any hydrogen ion exchange resin is useful in accordance with the principles of the present invention to provide a hydrogen enriched clay having reduced acid demand and better stability when suspended at a pH below about 6.0. Cross linked styrene-divinyl-benzene polymer has been found to give excellent hydrogen exchange since it possesses a high exchange capacity, has excellent stability and can be easily regenerated by acid contact.

EXAMPLE

Sodium carbonate in an amount of 1.5% by weight is mixed in water for about 5 minutes. A white montmorillonite (washed sodium bentonite) is slurried in the sodium carbonate treated water to a concentration of about 15% by weight bentonite. The clay is allowed to stand for about 1.5 hours to assure complete hydration and sodium ion exchange. A hydrogen ion exchange resin based on the following sulfonic-acid form of styrene-divinyl benzene copolymer:

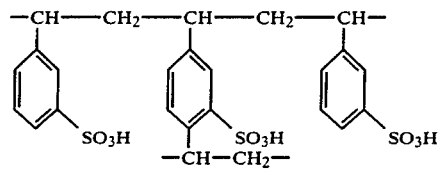

in bead form in an amount of 10% based on the weight of clay, is mixed into the clay slurry for a period of ½ hour at room temperature (70° F.). The slurry is then screened to remove the resin and the clay slurry is centrifuged and dried to about 8% moisture. Prior to hydrogen ion exchange, the white bentonite in a concentration of 3.5 grams in 500 milliliters of deionized water, requires 27 milliliters of 0.1 N HCl to reduce the pH to 4.0. After the above-described hydrogen ion exchange, the amount of 0.1 N HCl required was reduced to 13 milliliters. A Magnesium Aluminum Silicate composition meeting specifications, therefore, includes, for example, 70% of the above-described hydrogen ion exchanged bentonite (requiring 13 ml of 0.1 N acid/3.5 grams to reach a pH of 4.0; 20% hectorite requiring 13 ml. of 0.1 N acid/1.0 gram to reach a pH of 4.0) and 10% of saponite (requiring 3 ml of 0.1 N acid/0.5 gram to reach a pH of 4.0) making a total of 29 ml of acid to reach a pH of 4.0, well below the 40 ml. specification for acid demand. The composition has an Al/Mg ratio of about 1.0 and the proportions of clays can be varied significantly to provide a Magnesium Aluminum Silicate composition having an Al/Mg ratio within the full range of 0.5 to 5.5 to provide a product of any desired specification Type, while meeting acid demand and other specifications, such as viscosity and pH.

The amount of hydrogen ion exchange resin contacting the clay slurry, or residence time of the clay-resin contact can vary widely depending upon the amount of acid demand reduction desired and degree of clay contamination. Generally, the clay is slurried in water and mixed, screened to remove any grit or sand, centifuged and dried. The resin can be added to the clay prior to screening or after the centifuging. If it is added after the centifuging, the resin must be screened out prior to drying.

The amount of resin varies depending on the situation. For example, the white bentonite is generally contacted with about 10% resin based on the weight of the clay to assure that the acid demand specification will be met. In the case of saponite, for each pound of saponite, generally about five pounds of resin is used to assume sufficient ion exchange. Also, it is important that too much excess resin is not added so that when the slurry is dried, it does not fall out of final pH specifications of 9–10. Generally, the pH of the slurry during hydrogen ion exchange can be monitored and hydrogen ion exchange terminated when the pH of the slurry reaches a predetermined value, i.e. 9.0. The value is easily determined by minor trial and error to correlate pH of the slurry during hydrogen ion transfer to pH of the clay product after drying and slurrying in water.

I claim:

1. A water swellable clay composition having a pH of 9–10, a weight ratio of Aluminum to Magnesium of 0.5 to 5.5, and meeting existing acid demand specifications for Magnesium Aluminum Silicate comprising a montmorillonite and at least one other clay selected from the group consisting of saponite, hectorite, beidellite, and nontronite wherein at least one of said clays is hydrogen enriched by contacting said clay with a hydrogen ion exchange resin.

2. The water swellable clay composition of claim 1 wherein the composition has a weight ratio of Aluminum/Magnesium of 0.5 to 1.2.

3. The water swellable clay composition of claim 1 wherein the hydrogen enriched clay component has an acid demand reduced by at least 5% as a result of said hydrogen enrichment.

4. The water swellable clay composition of claim 3 wherein the acid demand of the hydrogen enriched clay component is reduced at least 10%.

5. The water swellable clay composition of claim 1 wherein the hydrogen enriched clay component has an acid demand reduced 10-60% as a result of the hydrogen enrichment.

6. The water swellable clay composition of claim 1 comprising 50 to 95% hydrogen enriched montmorillonite, and 5 to 35% hectorite.

7. The clay of claim 6 including 0.1 to 25% saponite.

8. The clay composition of claim 6 wherein the bentonite is sodium bentonite having 50 to 100 milliequivalents of sodium per 100 grams of clay.

9. The water swellable clay composition of claim 6 comprising 50 to 90% hydrogen enriched montmorillonite, 5 to 35% hectorite, and 0 to 20% saponite.

10. The water swellable clay composition of claim 9 comprising about 70% hydrogen enriched montmorillonite; about 20% hectorite and about 10% saponite, said composition meeting existing specifications for Magnesium Aluminum Silicate.

11. The clay composition of claim 9 wherein the montmorillonite is bentonite.

12. The water swellable clay composition of claim 1 wherein the composition meets the viscosity specification for Magnesium Aluminum Silicate.

13. The water swellable clay composition of claim 1 wherein the composition complys with all specifications for Magnesium Aluminum Silicate.

14. The clay composition of claim 1 wherein the montmorillonite is bentonite.

15. The clay composition of claim 14 wherein the bentonite is sodium bentonite having 50 to 100 milliequivalents of sodium per 100 grams of clay.

16. The clay composition of claim 15 including 0.1 to 25% saponite.

17. The composition of claim 1 wherein the hydrogen ion exchange resin is a sulfonic acid form of styrene-divinyl benzene.

18. A water swellable clay composition comprising about 70% hydrogen enriched bentonite; about 20% hectorite and about 10% saponite, said composition having a pH of 9-10, a weight ratio of Aluminum to Magnesium of 0.5 to 5.5, and meeting existing acid demand specifications for Magnesium Aluminum Silicate.

19. A water swellable clay composition comprising a mixture of dioctahedral smectite clay and a trioctrahedral smectite clay, at least one of said clays being hydrogen enriched by contacting said clay with a hydrogen ion exchange resin, said compositions having a pH of 9-10, a weight ratio of Aluminum to Magnesium of 0.5 to 5.5, and meeting existing acid demand specifications for Magnesium Aluminum Silicate.

* * * * *